United States Patent
Nakayama et al.

(10) Patent No.: US 8,475,395 B2
(45) Date of Patent: Jul. 2, 2013

(54) PAINLESS BLOOD-COLLECTING METHOD

(76) Inventors: Toru Nakayama, Tokyo (JP); Mariko Nakayama, Tokyo (JP); Masafumi Nakayama, Tokyo (JP); Takayuki Nakayama, Tokyo (JP)

(*) Notice: Subject to any disclaimer, the term of this patent is extended or adjusted under 35 U.S.C. 154(b) by 1058 days.

(21) Appl. No.: 10/544,431

(22) PCT Filed: Feb. 12, 2004

(86) PCT No.: PCT/JP2004/001501
§ 371 (c)(1),
(2), (4) Date: May 25, 2006

(87) PCT Pub. No.: WO2004/078041
PCT Pub. Date: Sep. 16, 2004

(65) Prior Publication Data
US 2006/0224085 A1      Oct. 5, 2006

(30) Foreign Application Priority Data
Feb. 13, 2003   (JP) .................................. 2003-74592

(51) Int. Cl.
*A61B 5/00* (2006.01)
(52) U.S. Cl.
USPC ........................................................ 600/583
(58) Field of Classification Search
USPC ..................... 600/573, 583; 606/181–183
See application file for complete search history.

(56) References Cited

U.S. PATENT DOCUMENTS

| | | | | |
|---|---|---|---|---|
| 4,547,735 A | * | 10/1985 | Kiesewetter et al. | 324/450 |
| 5,035,704 A | * | 7/1991 | Lambert et al. | 606/182 |
| RE35,803 E | * | 5/1998 | Lange et al. | 606/182 |
| 6,155,992 A | | 12/2000 | Henning et al. | |
| 6,350,273 B1 | | 2/2002 | Minagawa et al. | |
| 6,840,912 B2 | | 1/2005 | Kloepfer et al. | |
| 2002/0169393 A1 | * | 11/2002 | Cunningham et al. | 600/573 |

FOREIGN PATENT DOCUMENTS

EP   1 421 899   5/2004

OTHER PUBLICATIONS

Kudo, Kunimasa, Illustrated Phlebotomy Procedure, Japan 1980, p. 68, line 19-p. 69, line 16.

* cited by examiner

*Primary Examiner* — Max Hindenburg
*Assistant Examiner* — Jonathan M Foreman
(74) *Attorney, Agent, or Firm* — Burr & Brown

(57) ABSTRACT

A method is provided for collecting a small blood sample by painlessly puncturing a finger. When the skin of a human being is punctured by a needle or another device at the depth that does not exceed 0.5 mm, pain accompanying the puncture is diminished or decreased. Regardless of an error in the depth of the puncture, the depth of puncture must not exceed this depth. The puncture site is located on the dorsal surface of a finger, in the area from the finger joint (IP joint of thumb, DIP joint of fingers other than thumb) to the proximal nail wall and the area extending from the proximal nail wall to the lateral nail wall.

2 Claims, 1 Drawing Sheet

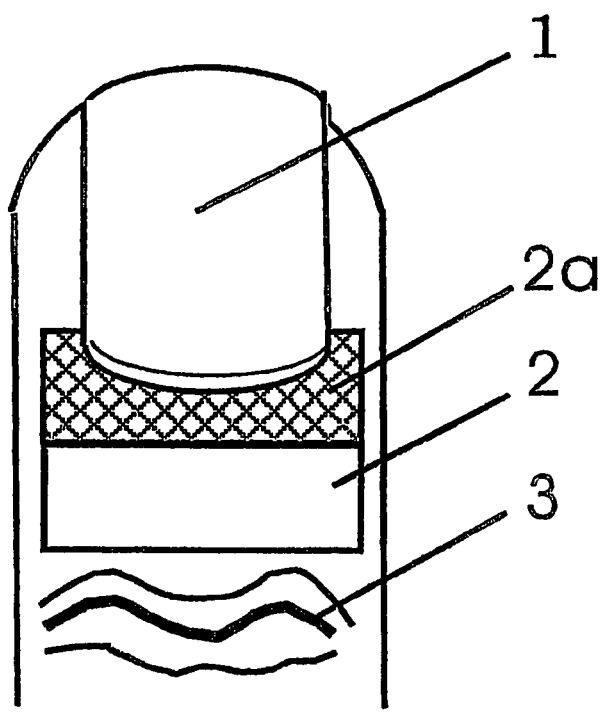

PAINLESS BLOOD-COLLECTING METHOD

BACKGROUND OF THE INVENTION

1. Field of the Invention

This invention relates to a method for collecting a small blood sample by painlessly puncturing fingers of a hand.

2. Prior Art

Self monitoring of blood glucose (SMBG) for diabetic patients has been performed using blood obtained by needle puncture of the finger tips (palm side, lateral side), which contain many pain spots. The depth of puncture achieved by puncture devices used for SMBG is preferably in the range of 0.5 mm to 2.0 mm. Moreover, the range of 0.7 mm to 1.3 mm has been considered to be particularly important (refer to U.S. Pat. No. 5,318,584). Moreover, the error in the depth of puncture has been known to be more than ±0.3 mm (refer to U.S. Pat. No. 5,318,584). According to the conventional technique, pain accompanied with puncture of finger tips can not be avoided, because the puncture is performed at a site having many pain spots, and because the depth of the puncture is deep. Recently, attempts to avoid pain accompanied with blood collection have been made by performing punctures at abdominal areas or on the forearm, which have comparatively fewer pain spots. However, complete elimination of pain can not be realized by using this method. Moreover, delayed alteration in blood glucose level measured by puncture of forearm compared with fingertip has been reported. Therefore, there has been a demand for the development of a painless method for collecting blood from the fingers.

SUMMARY OF THE INVENTION

This invention relates to a method for collecting blood with decreased pain, by puncturing fingers at a site having few pain spots at a shallow depth.

The area of puncture: At present, when collecting blood from finger tips, puncture of the dorsal surface of a finger has not been recommended to patients, despite having less pain spots. According to present invention, the area of a finger approximate to the nail root is adopted for the site of blood collection, because the area has an abundant blood-stream and bleeds easily. According to this invention, the area of puncture in the dorsal (i.e., top surface opposing the palm side) surface of a finger is the area from finger joint (IP joint of thumb, DIP joint of fingers other than thumb) to proximal nail wall and the area extending from proximal nail wall to lateral nail wall (FIG. 1: 2). The most preferred area for puncture is the proximal nail wall area and the area extending from the proximal nail wall to the lateral nail wall (FIG. 1: 2a).

The depth of puncture: The thickness of the skin epidermis of a body, except for palma manus and planta pedis, is from 0.07 mm to 0.12 mm. The skin epidermis of palma manus and that of planta pedis are more thick, reaching 0.8 mm for palma manus and 1.4 mm for planta pedis. The dermis underlies downside of the epidermis. Just under the dermis, there are blood vessels such as dermal papillary loops and subpapillary plexus. Free nerve endings are involved in pain sensation entries from the epidermis to the dermis. Therefore, in order to achieve skin puncture with decreased pain, the depth of puncture needs to be set at the minimal depth that can injure a blood vessel existing just downside of the dermis. If the depth of the puncture is shallow, the damage to the skin tissue decreases. Considering the matters described above, skin puncture was performed on the fingers of volunteers at the depths of 0.2, 0.3, 0.4, 0.5 and 0.6 mm (as described below).

As a result, it was determined that the depth of puncture that enables painless puncture is no more than 0.5 mm. Even if some error occurs on the depth of puncture, it is necessary that the depth of puncture always does not exceed this range.

BRIEF EXPLANATION OF THE DRAWINGS

FIG. 1 shows the site of puncture on the dorsal surface of a finger. The explanation of the numerals used in the drawing is as follows:
(1) nail; (2) site of puncture; (2a) the most preferred site for puncture; and (3) finger joint (IP joint of thumb, DIP joint of fingers other than thumb).

DETAILED DESCRIPTION OF THE INVENTION

The method to obtain blood sample from the site of puncture: In many cases, a sufficient amount of blood can not be obtained only by puncturing the skin, when the depth of the puncture is shallow according to this invention. In that case, after performing puncture to a finger, congestion at the site of puncture may be achieved, for example by inflecting the finger joint (IP joint of thumb, DIP joint of fingers other than thumb) of the punctured finger, by making compression or avascularization at a proximal area from the puncture site on the finger, or by compressing finger tip of the punctured finger, whereby bleeding is enhanced.

Example

To determine the puncture depth that enables painless puncture, punctures were performed at the puncture site described above using various puncture depths. A puncture device provided by TERUMO (Medisafe Fine Touch) was converted for shallow puncture. Using this device, skin puncture was performed at the depths of 0.2, 0.3, 0.4, 0.5 and 0.6 mm. Error on the puncture depth was ±0.13 mm at the maximum. Blood glucose was measured using the blood obtained by the skin puncture. A device for SMBG provided by TERMO (Medisafe Voice) was used to determine the blood glucose. According to this device, a blood sample of 2 µl is needed for measurement of blood glucose.

Thirty-five healthy volunteers participated in this investigation. For each of five fingers randomly selected for each volunteer, the puncture depths of 0.2, 0.3, 0.4, 0.5 and 0.6 mm were assigned randomly. When the puncture depth was 0.2 mm, two punctures were needed to measure the blood glucose of two volunteers. As to other volunteers, it was possible to measure the blood glucose with one puncture. Among the thirty-five volunteers, 31 volunteers (89%) with a puncture depth of 0.2 mm, 33 volunteers (94%) with a puncture depth of 0.3 mm, 23 volunteers (66%) with a puncture depth of 0.4 mm, 16 volunteers (46%) with a puncture depth of 0.5 mm, and 6 volunteers (17%) with a puncture depth of 0.6 mm did not feel any pain. Compared with the puncture depth of 0.2 mm, the ratio of individuals who felt no pain decreased significantly when the puncture depth was more than 0.4 mm. As the result of this investigation, it was determined that in order to puncture fingers without pain, it is necessary to use a puncture depth of no more than 0.5 mm, including error.

INDUSTRIAL APPLICABILITY

The painless method for collecting blood according to this invention is not only useful to decrease pain of the subject during the collecting of blood, but the method is also advantageous with respect to medical economics. When another portion of body, other than a finger, is punctured for blood collection, aspiration of blood using a vacuum pump from the puncture site may be needed to obtain the blood sample. However, in the method of collecting blood according to this invention, a device such as a vacuum pump is not needed. Moreover, to perform SMBG, a conventional and widely used device for blood glucose measurement may be utilized without modification. Therefore, this invention provides a painless system for measuring blood glucose for many diabetic patients at low cost.

What is claimed is:

1. A method for collecting blood with little pain, comprising:

forming a puncture at a puncture site of a finger of a human being by one of a needle and another puncturing device, wherein
    (a) a depth of the puncture is no more than 0.4 mm, and
    (b) the puncture site is located on the dorsal surface of a finger and is defined by an area from a finger joint to a proximal nail wall and the area extending from the proximal nail wall to a lateral nail wall, wherein the finger joint is one of an IP joint of a thumb and a DIP joint of a finger other than the thumb; and enhancing bleeding by applying persistent positive pressure using a method selected from the group consisting of inflecting the finger joint of the punctured finger, asserting compression or avascularization at a proximal area from the puncture site on the finger, and compressing a tip of the punctured finger.

2. The method for collecting blood with little pain according to claim 1, wherein the depth of the puncture is not more than 0.3 mm.

* * * * *